United States Patent [19]

Monchalin

[11] Patent Number: 4,633,715
[45] Date of Patent: Jan. 6, 1987

[54] LASER HETERODYNE INTERFEROMETRIC METHOD AND SYSTEM FOR MEASURING ULTRASONIC DISPLACEMENTS

[75] Inventor: Jean-Pierre Monchalin, Montreal, Canada

[73] Assignee: Canadian Patents and Development Limited - Societe Canadienne des Brevets et d'Exploitation Limitee, Ottawa, Canada

[21] Appl. No.: 731,733

[22] Filed: May 8, 1985

[51] Int. Cl.$^4$ ............................................. G01N 29/00
[52] U.S. Cl. ........................................ 73/657; 73/643; 73/655; 356/358
[58] Field of Search ..................... 73/655, 657, 643; 356/358

[56] References Cited

U.S. PATENT DOCUMENTS

| | | | |
|---|---|---|---|
| 4,180,328 | 12/1979 | Drain | 73/657 |
| 4,313,185 | 1/1982 | Chovan | 73/657 |
| 4,381,676 | 5/1983 | Kaule et al. | 73/657 |
| 4,388,832 | 6/1983 | Kaule | 73/655 |
| 4,512,661 | 4/1985 | Claus | 73/657 |
| 4,581,939 | 4/1986 | Takahashi | 73/655 |

*Primary Examiner*—Howard A. Birmiel
*Attorney, Agent, or Firm*—Schwartz, Jeffery, Schwaab, Mack, Blumenthal & Evans

[57] ABSTRACT

The invention is concerned with a laser heterodyne interferometric method and system for measuring the displacement of a free surface of a material subjected to ultrasound. A laser beam having a predetermined intensity is generated and then divided into first and second beam portions having respective intensities representing minor and major fractions of the predetermined intensity, the first beam portion being angularly displaced relative to the second beam portion and being frequency shifted by a predetermined frequency. The second beam portion is passed through an optical lens off-center thereof to focalize the second beam portion onto the free surface of the material subjected to ultrasound, thereby scattering same. The scattered second beam portion is combined with the first beam portion to obtain an optical fringe signal which is converted into an electrical fringe signal comprising a central peak at the predetermined frequency and a sideband on either side of the central peak. The electrical fringe signal is thereafter processed through circuitry means without demodulating a phase modulation produced by ambient vibrations, to extract a signal proportional to the displacement of the free surface.

26 Claims, 5 Drawing Figures

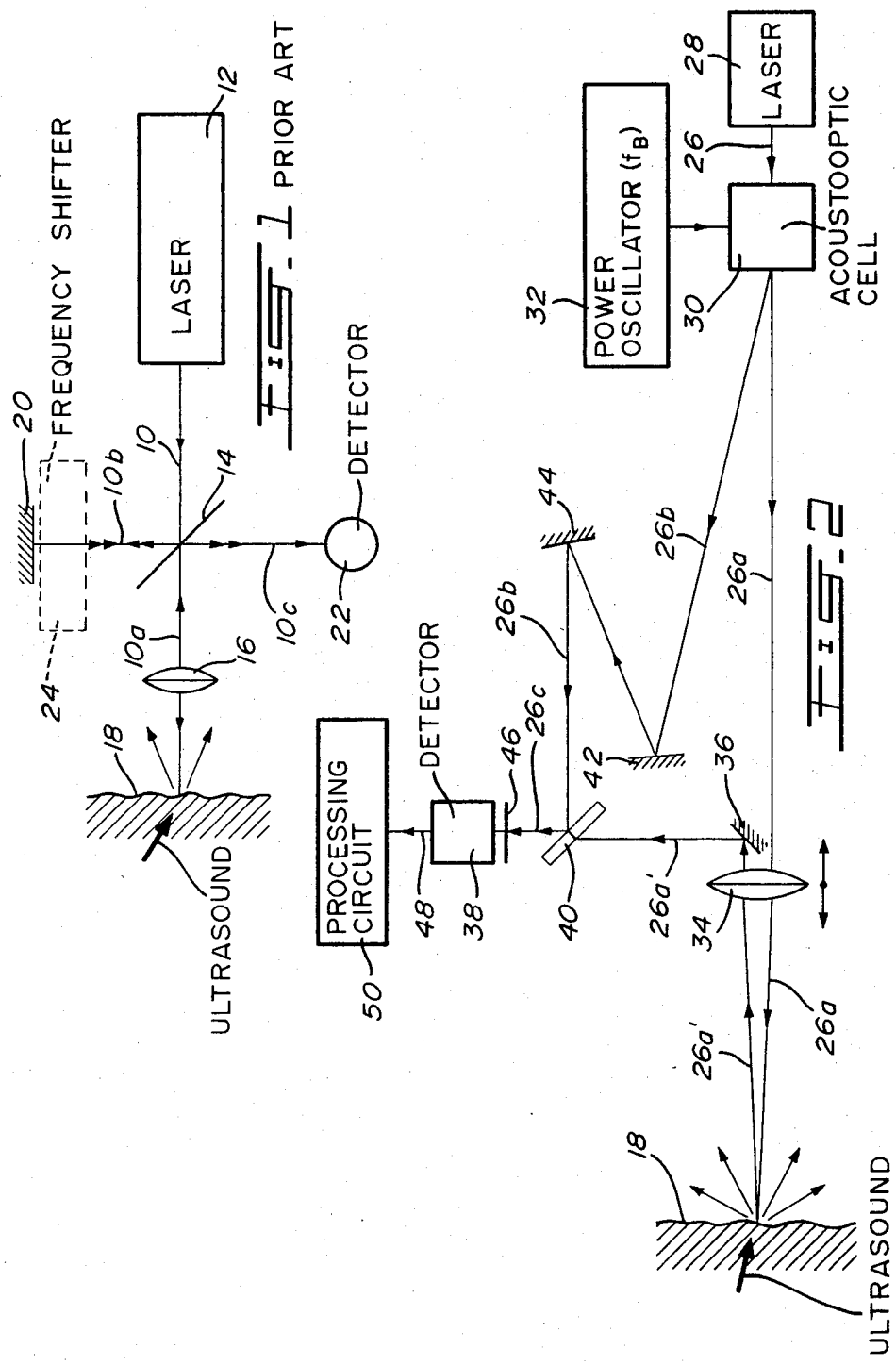

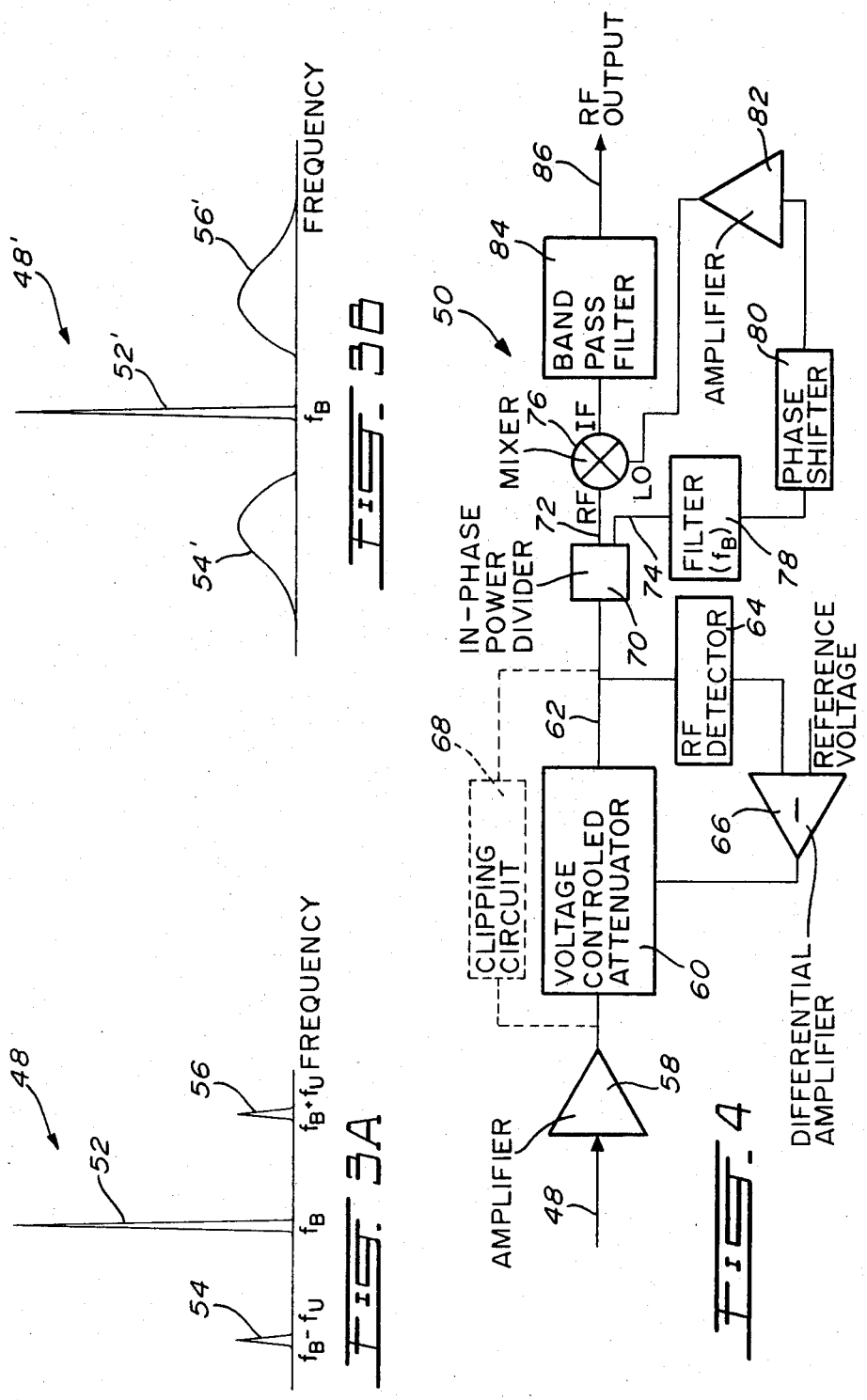

LASER HETERODYNE INTERFEROMETRIC METHOD AND SYSTEM FOR MEASURING ULTRASONIC DISPLACEMENTS

BACKGROUND OF THE INVENTION

The present invention relates to a laser heterodyne interferometric method and system for measuring ultrasonic displacements. The invention is particularly directed toward measuring in a reliable and convenient manner the small displacements of the free surface of a workpiece subjected to ultrasound.

In present industry, quality control is very important. Among the different techniques used for testing manufactured products, ultrasonic methods are the most suitable. These are generally based on the launching of an ultrasonic transient wave inside the material to be tested using a piezoelectric transducer brought into contact with the material and receiving by means of the same transducer an echo coming from a surface of the material or from within the sample itself. This echo may be indicative of a defect inside the sample or in the case of a defect-free material where the echo (or echo sequence) is produced by a back surface of the sample, such echo may be used to derive information on properties of the material, such as grain size, porosity, different phases and residual stresses. In practice, the ultrasonic wave produced by the transducer may not be uniform or may have an inappropriate time variation which will strongly affect the accuracy of the ultrasonic inspection.

The surface deformations or displacements of a material produced by an ultrasonic piezoelectric transducer occur in the range of frequencies extending from 0.5 MHz to 50 MHz at most. High ultrasonic frequencies are generally strongly attenuated by currently used engineering materials so the frequencies of interest generally do not exceed 15 MHz. The displacements are generally much less than an optical visible wavelength (5000 Å) and range from a fraction of 1 Å to a few hundred Å at most.

In order to check or characterize a piezoelectric transducer or to obtain a quantitative measurement of the surface displacement of a workpiece subjected to ultrasound, an optical interferometric probe is advantageously used. A known design is basically a Michelson interferometer which senses directly the surface displacement since one of the mirrors of the interferometer is constituted by the surface itself. The light source is a laser which produces a nearly collimated beam. Since the surface is not generally polished but is rough, good contrast interference fringes are only observed when the surface is set at the focus of a lens. Such a system is limited in use for best detection conditions to only one of the speckle spots scattered by the surface. Therefore, in practice, most of the incident light intensity is wasted and depending upon the surface scattering properties and the lens numerical aperture, only a small fraction of the intensity is used for interference. As a result, such an interferometric probe may lack adequate sensitivity.

It is also important to note that in the above interferometric probe the phase difference between the two interferring beams and therefore the detected signal are strongly affected by ambient vibrations which occur at frequencies mostly in the audio-range (<100 KHz) but with amplitudes which can exceed one optical wavelength. Various solutions have already been proposed to solve this problem in both the homodyne interferometric probes (in which the optical frequency is the same in both arms of the interferometer) and heterodyne interferometric probes (in which the optical frequency in one arm has been shifted by $f_B$ by means of a Bragg or acoustooptic cell and the interference signal appears at the shift frequency $f_B$).

For instance, in several homodyne interferometric probes, the path length change caused by ambient vibrations is compensated by moving the reference mirror. The error signal used for compensation can be obtained by dithering the reference mirror and phase detection or by finding the reference voltage level corresponding to maximum sensitivity. Such systems which rely on active stabilization do not work well in an industrial environment where the vibration level is high and are limited to laboratory experimentations. Using a different design called quadrature-dual interferometer, where the Michelson interferometer is slightly modified by adding a birefringent plate, and by using two detectors, it is possible to derive a signal independent of ambient vibrations. In this system, one detector records a signal varying in proportion to the sine of the optical path difference whereas the other measures a signal varying as its cosine. By squaring these two signals, the sensitivity to ambient vibrations is removed. This system has the drawback of requiring to square a signal at a frequency of a few MHz which is in practice difficult. Another drawback is the use of two detectors which should be adjusted to see the same part of the fringe pattern and have their outputs amplified to the same level; thus, any slight change in the set-up will affect the operation.

Several heterodyne interferometric systems have been previously described and two commercial versions are known to exist. In such systems, the ultrasonic displacement produces a phase modulation of the optical beam impinging upon the probed surface. After mixing with the beam which is reflected by the reference mirror and whose frequency is shifted by $f_B$, $f_B$ being much larger than the ultrasonic frequencies involved, a varying intensity signal $I_D$ called the fringe signal is detected at the output of the interferometer and is given by the following relation:

$$I_D = 2I_L \sqrt{R} \sqrt{S} \cos[2\pi f_B t - 4\pi \delta_s(t)/\lambda + \phi(t)] \quad (1)$$

Where
 $I_L$ is the laser intensity;
 R is the effective transmission coefficient in intensity for the reference beam;
 S is the effective transmission coefficient in intensity for the beam reflected off the surface (S is much less than unity);
 $f_B$ is the shift frequency;
 $\delta_s(t)$ is the surface displacement as a function of time t;
 $\lambda$ is the optical wavelength; and
 $\phi(t)$ is a phase factor which depends upon the interferometer path difference and is affected by ambient vibrations.

Since $\delta_s(t)$ is much less than $\lambda$, one can write:

$$I_D \sim 2I_L \sqrt{R} \sqrt{S} \cos\left[(2\pi f_B t + \phi(t)) + \right. \quad (2)$$

-continued $$\left. \frac{4\pi\delta_s(t)}{\lambda} \sin(2\pi f_B t + \phi(t)) \right]$$

which shows that the ultrasonic displacement causes a weak sideband on either side of a central peak at the shift frequency $f_B$. The absolute value of the displacement can be readily determined from the magnitude of the side bands compared to that of the central peak; this is an advantage of an heterodyne interferometric probe over an homodyne one for which a real time absolute measurement is not directly possible.

A commercially available heterodyne interferometric probe manufactured by the Disa Company is limited to frequencies below 1 MHz and relatively large displacements. Its field of application is actually the measurement of ambient vibrations. On the other hand, in the heterodyne interferometric probe developed by the Nondestructive Testing Centre of the Atomic Energy Research Establishment (Harwell) in England, ambient vibrations are continuously compensated by varying the shift frequency $f_B$ in such a way that the overall phase $2\pi f_B t + \phi(t)$ is unaffected by the vibrations. However, such a probe is complex and very expensive.

Several systems are also known which use a VHF receiver tuned to one of the side bands of the fringe signal. They are insensitive to ambient vibrations but are limited to only continuous ultrasonic displacements, and the phase of the displacement is lost.

SUMMARY OF THE INVENTION

It is therefore an object of the present invention to overcome the above drawbacks and to provide a laser heterodyne interferometric method and system for measuring in a reliable and convenient manner the surface displacement of a material subjected to ultrasound.

It is a further object of the invention to provide such a heterodyne interferometric measuring method and system having improved sensitivity while being insensitive to ambient vibrations so as to obtain a vibration-free signal corresponding to a variation in time of the surface displacement, which after calibration, can provide an absolute value of the true displacement of the surface.

In accordance with a first aspect of the invention, there is thus provided a laser heterodyne interferometric method for measuring the displacement of a free surface of a material subjected to ultrasound, which comprises the steps of:

(a) generating a laser beam having a predetermined intensity;

(b) dividing the laser beam into first and second beam portions having respective intensities representing minor and major fractions of the predetermined intensity, the first beam portion being angularly displaced relative to the second beam portion and being frequency shifted by a predetermined frequency;

(c) passing the second beam portion through an optical lens off-center thereof to focalize the second beam portion onto the free surface of the material subjected to ultrasound, thereby scattering same;

(d) combining the scattered second beam portion with the first beam portion to obtain an optical fringe signal;

(e) converting the optical fringe signal into an electrical fringe signal comprising a central peak at the predetermined frequency and a sideband on either side of the central peak; and (f) processing the electrical fringe signal through circuitry means without demodulating a phase modulation produced by ambient vibrations, to extract a signal proportional to the displacement of the free surface.

According to a preferred embodiment, the first and second beam portions are caused to travel along respective optical paths having substantially the same length. Use can be made for instance of a first mirror for reflecting the first beam portion and a second mirror for directing the reflected first beam portion to a beam mixer where it is combined with the scattered second beam portion, the first and second mirrors being movable relative to one another to vary the optical path length of the first beam portion in accordance with the optical path length of the second beam portion.

According to another preferred embodiment of the invention, the electrical fringe signal obtained in step (e) is processed by passing such a signal through an in-phase power divider to divide the signal into first and second signal components, passing the first signal component through a narrow band filter to reject the sidebands without demodulating the phase modulation produced by ambient vibrations and then through a phase shifter to produce a total phase shift of $\pm 90°$, mixing the filtered and phase shifted first signal component with the second signal component and passing the resulting signal through a band-pass filter to remove DC and high frequency components and thereby obtain a signal proportional to the surface displacement. The electrical fringe signal prior to being passed through the in-phase divider preferably has an amplitude which is maintained substantially constant.

The present invention also provides, in a further aspect thereof, a laser heterodyne interferometric system for carrying out a method as defined above, which system comprises:

laser source means for generating a laser beam having a predetermined intensity;

beam dividing means for dividing the laser beam into first and second beam portions having respective intensities representing minor and major fractions of the predetermined intensity, the first beam portion being angularly displaced relative to the second beam portion and being frequency shifted by a predetermined frequency;

an optical lens disposed to receive off-center thereof the second beam portion for focalizing the second beam portion onto the free surface of said material subjected to ultrasound, thereby scattering same;

beam mixing means for combining the scattered second beam portion with the first beam portion to obtain an optical fringe signal;

detector means for converting the optical fringe signal into an electrical fringe signal comprising a central peak at the predetermined frequency and a sideband on either side of the central peak; and circuitry means for processing the electrical fringe signal without demodulating a phase modulation produced by ambient vibrations, to extract a signal proportional to the displacement of the free surface.

The beam dividing means preferably comprises an acoustooptic cell such as a Bragg cell which is driven at the predetermined frequency, for example, 40 MHz.

On the other hand, the circuitry means used for processing the electrical fringe signal preferably comprise an in-phase power divider having an input and first and second outputs, the input of the divider being connected to the detector means for dividing the electrical fringe signal into first and second signal components. A narrow band filter with an input and an output has its input connected to the first output of the divider for filtering the first signal component to reject said sidebands without demodulating the phase modulation produced by ambient vibrations. A phase shifter with an input and an output has its input connected to the output of the narrow band filter for producing a total phase shift of ±90°. A mixer with first and second inputs and an output has its first and second inputs connected respectively to the output of the phase shifter and to the second output of the divider for mixing the filtered and phase shifted first signal component with the second signal component. There is also included a band-pass filter having an input and an output, the input of the band-pass filter being connected to the output of the mixer for filtering the resulting signal to remove DC and high frequency components and thereby obtain a signal proportional to the surface displacement.

The laser heterodyne interferometric method and system of the invention can be used in several applications, among which are ultrasonic field mapping and characterization of ultrasonic transducers. For example, the system of the invention can be used to scan over the front surface of a compression transducer to observe the true surface displacement occurring in time and at different locations over the whole surface of the transducer. It can also be used to scan the ultrasonic field actually produced on a workpiece. In an example of application which is encountered in many practical circumstances, a transducer with an acoustic lens is mounted on a curved sample (e.g. part of a pipeline). This transducer and its lens ("focused transducer") are designed to produce a focal spot size sufficiently small to give appropriate resolution. The system of the invention measures the vertical displacement produced when the generated inclined shear wave impinges on the outer or inner surface. By scanning, one can measure the actual spot size on the surface (in both directions), including the amplitude of any lobe near the main focus. From the amplitude and phase distribution measured by such a scan, the ultrasonic field distribution over any plane or surface in the workpiece can be calculated. If the transducer has been designed for detecting a defect at some depth inside the workpiece, a test sample with a thickness equal to the depth can be used, which gives directly the beam size information. Such an application will be in practice very useful, since ultrasonic probes are never constructed exactly as designed, important variations may exist between actual and calculated parameters, besides parasitic lobes possibly occurring.

The system of the invention also has the advantage over conventional ultrasonic transducers to have a wide bandwidth, a very high spatial resolution and to be non-contacting. Therefore, it can be advantageously used to detect acoustic emission displacement pulses and ultrasound generated by a laser pulse.

BRIEF DESCRIPTION OF THE DRAWINGS

Further features and advantages of the invention will become more readily apparent from the following description of preferred embodiments with reference to the appended drawings, in which:

FIG. 1 is a schematic diagram of a Michelson-type interferometric probe according to the prior art;

FIG. 2 is a schematic diagram of a heterodyne interferometric probe according to the invention;

FIGS. 3A and 3B show the RF spectrums of the output signals at the detector in FIG. 2, when the workpiece is subjected to continuous and pulse ultrasonic excitations, respectively; and FIG. 4 is a schematic diagram of the electronic circuit used for processing the signals shown in FIG. 3.

DESCRIPTION OF PREFERRED EMBODIMENTS

Referring first to FIG. 1 which schematically illustrates a Michelson-type interferometric probe according to the prior art, a laser beam 10 generated by the laser source 12 is directed onto a beam splitter 14 and split into two beam portions 10a and 10b. The beam portion 10a is passed through the center of an optical lens 16 which focalizes it onto the free surface 18 of a material or workpiece subjected to ultrasound. The ultrasonic displacement of the probed surface 18 can be produced by an ultrasonic piezoelectric transducer or other means such as electrical discharge, projectile impact or high intensity laser pulse; it can also occur naturally in a strained material (the so-called acoustic emission phenomena). The surface 18 acts as one of the mirrors of the interferometer and reflects a portion of the scattered beam back onto the beam splitter 14. The beam portion 10b, on the other hand, is directed onto the reference mirror 20 which reflects it back to the beam splitter 14 so as to be combined with the scattered beam portion coming from the surface 18, the combined beam portions 10c interferring with one another to produce a fringe signal which is detected by the detector 22. A frequency shifter 24 can optionally be located in the optical path of the beam portion 10b so as to shift the frequency of the latter by a predetermined value, thereby converting the system from a homodyne to a heterodyne interferometer.

As previously mentioned, since the surface 18 is not generally polished but is rough and scatters incident light, so most of the light energy is wasted, the probe may lack adequate sensitivity. It is therefore important to have an optical configuration which ensures that the available laser power is used in such a way to meet the best detection conditions. Since the reference beam of an interferometer is generally more intense than the beam reflected off the probed surface of a workpiece and contributes almost exclusively to the quantum noise of detection, the best conditions are obtained when the intensity of the beam reflected off the surface and reaching the detector has been maximized for a given laser intensity. Previously known designs have the drawbacks of not fulfilling this requirement.

The requirement mentioned above is satisfied by a laser heterodyne interferometric system according to the invention, which is schematically represented in FIG. 2. As shown, the laser beam 26 generated by the laser source 28 is sent through an acoustooptic cell 30, such as a Bragg cell, driven at the frequency $f_B$ by a power RF oscillator 32 tuned to the frequency $f_B$; the frequency $f_B$ can be for example 40 MHz. To meet the above requirement, the adjustment of the cell 30 and the power level from the oscillator 32 are such that most of the light goes through as a beam portion 26a and that only a small fraction (about 10% or less) is angularly deflected as a beam portion 26b which is frequency shifted by $f_B$. The undeflected and unshifted beam portion 26a is sent directly onto the probed surface 18 through an optical lens 34 off-center thereof which focalizes the beam portion 26a onto the surface 18 where it is scattered. The lens 34 is used off center in order to enable to pick-up the scattered beam portion 26a' with a small mirror 36; the use of the lens 34 on center would require an additional beam splitter and result in wasting half of the available light intensity. The scattered beam portion 26a' which is used for interference is reflected by the mirror 36 and sent to the detector 38 through a beam mixer 40. Since in practice the beam portion 26a' coming from the surface 18 is weak, optimum use of the available light intensity requires a high transmitting beam mixer. This condition is easily fulfilled by using an uncoated glass slab which transmits over 90% of the incoming intensity. The frequency-shifted beam portion 26b (i.e. reference beam) is picked-up by mirrors 42 and 44 and directed onto the beam mixer 40 where a small fraction (about 10% for a polarization perpendicular to the plane of the drawing) is reflected by the latter and combined with the scattered beam portion 26a', the combined beam portions 26c interferring with one another to produce an optical fringe signal which is detected by the detector 38. The detector 38 can be a photodiode which converts the optical fringe signal into an electrical fringe signal 48; it is advantageously located behind a narrow band interference filter 46 matched to the laser used, for improving detection. The electrical fringe signal 48 is thereafter processed through an electronic circuit 50 to extract a signal proportional to the surface displacement.

In order to observe the fringe signal, the beam mixer 40 should be properly oriented and the beam portion 26a brought into focus on the probed surface 18. This last adjustment ensures a mean speckle spot size on the lens 34 of the order of the size of the incident beam and maximizes the amplitude of the fringe signal. A laser operating on $TEM_{oo}$ modes will give best results, but it does not have to run on a single longitudinal mode. In the case of a multimode laser, it can be shown that all the modes add up their contribution to the fringe signal independently of the optical path length difference, if the path length difference between the arms of the interferometer is substantially equal to zero or an integer times twice the laser cavity length. In the system shown in FIG. 2, a near zero path length difference is obtained from the folded reference beam configuration produced by the mirrors 42 and 44. These mirrors are advantageously movable relative to one another to vary the optical path length of the beam portion 26b in accordance with the optical path length of the beam portions 26a and 26a' such that both optical path lengths are substantially the same.

In practice, good results can be obtained with low power He-Ne lasers (5 mw) at close working distances (a few ten centimeters). Better results are obtained with higher power lasers such as the neodymium-YAG continuous laser (typically 1 w) and the continuous $Ar^+$ laser (typically several w). Since with this system a parth length difference close to zero can be readily obtained, laser diodes can be used as well.

The electrical fringe signal 48 at the output of the detector 38 is represented in FIG. 3. When the material or workpiece is subjected to a continuous ultrasonic excitation at the frequency $f_U$ (FIG. 3A), the electrical fringe signal 48 is seen to comprise a central peak 52 at the shift frequency $f_B$ and two sidebands 54 and 56, one on either side of the peak 52. In the case of a pulse excitation (FIG. 3B), the electrical fringe signal 48' obtained also comprises a central peak 52' at the frequency $f_B$ and two sidebands 54' and 56', but the sidebands are broadened.

Turning to FIG. 4 which schematically represents the processing circuit 50 used for extracting from the electrical fringe signal a signal proportional to the surface displacement, independently from vibrations, the amplitude of the electrical fringe signal 48 is first maintained constant and this can be done by passing the signal 48 through a voltage controlled amplifier consisting of a fixed gain amplifier 58 having its output coupled to a voltage controlled attenuator 60 so as to produce a signal 62 at a fixed preset level suitable for further processing. The signal level is measured by a RF detector 64, the output of which is compared to a DC reference voltage by means of the differential amplifier 66. The differential voltage from the amplifier 66 is then applied to the attenuator 60 in order to produce the desired signal level. Alternatively, it is possible to amplify the electrical fringe signal 48 to a high level by means of the amplifier 58 and then to limit its amplitude using a clipping circuit 68 shown in broken lines. The maintaining of a substantially constant signal amplitude is effected because the amplitude of the scattered beam in the direction of the reference beam and therefore the fringe amplitude could vary greatly because of the speckle phenomenon. Changes of the speckle pattern can be seen by moving the beam focal joint over the probed surface 18 (FIG. 2). When a brighter speckle coincides with the reference beam (and therefore the detector aperture), a higher fringe signal is observed.

Following this amplification stage, the signal 62 is passed through an in-phase power divider 70 so as to divide the signal in two in-phase components 72 and 74. The signal component 72 is sent directly to the RF port of a RF mixer 76. The other signal component 74 is first filtered by means of a narrow band filter 78 having a bandwidth of 0.5 to 1 $MHz$, which rejects the sidebands 54 and 56 (FIG. 3). This filter should not be too narrow or the phase modulation produced by ambient vibrations would be demodulated and would cause an adversed amplitude fluctuation of the central peak 52 at the shift frequency $f_B$. The filtered signal which includes only the peak at the frequency $f_B$ is then passed through an adjustable phase shifter 80 so as to obtain a signal proportional to $\sin(2\pi f_B t + \phi(t))$, which is amplified to an appropriate level by the amplifier 82 before being applied to the LO port of the mixer 76. The phase shifter 80 is adjusted such that the total phase shift produced by the filter 78 and the phase shifter 80 at the frequency $f_B$ is equal to $\pm 90°$. By reference to equation (2), the IF output of the mixer 76 shows constant terms, terms at 2 $f_B$ and a term proportional to the surface displacement $\delta(t)$. Following band-pass filtering by means of the filter 84 having a bandwidth of 0.5 to 20 MHz to remove DC and high frequency components and to thus eliminate the constant and 2 $f_B$ terms, a signal 86 proportional to the surface displacement $\delta(t)$ is obtained at the RF output.

Calibration of the probe can be easily performed by probing a material which is subjected to continuous ultrasonic excitation at a frequency $f_U$ and set into resonance at this frequency. Then, by using a RF spectrum analyser which displays the electrical fringe signal as shown in FIG. 3A, the ratio of the amplitude of the sidebands 54 and 56 to that of the central peak 52 at the frequency $f_B$ is measured. This ratio which is equal to $2\pi A/\lambda$ where A is the displacement amplitude ($\delta(t) = A \cos 2\pi f_U t$) enables to measure the displacement amplitude A. Using then the probe electronic processing circuitry 50, the RF output signal can be measured giving the calibration of the probe in volts/Å of displacement, for a given reference DC voltage. This is performed once for all, i.e. the instrument can be factory calibrated.

I claim:

1. A laser heterodyne interferometric method for measuring the displacement of a free surface of a material subjected to ultrasound, which comprises the steps of:
   (a) generating a laser beam having a predetermined intensity;
   (b) dividing said laser beam into first and second beam portions having respective intensities representing minor and major fractions of said predetermined intensity, said first beam portion being angularly displaced relative to said second beam portion and being frequency shifted by a predetermined frequency;
   (c) passing said second beam portion through an optical lens off-center thereof to focalize said second beam portion onto the free surface of said material subjected to ultrasound, thereby scattering same;
   (d) combining the scattered second beam portion with said first beam portion to obtain an optical fringe signal;
   (e) converting said optical fringe signal into an electrical fringe signal comprising a central peak at said predetermined frequency and a sideband on either side of said central peak; and
   (f) processing said electrical fringe signal through circuitry means without demodulating a phase modulation produced by ambient vibrations, to extract a signal proportional to the displacement of said free surface.

2. A method as claimed in claim 1, wherein the respective intensities of said first and second beam portions represent approximately 10% and 90% of said predetermined intensity.

3. A method as claimed in claim 1, wherein step (b) is carried out by passing said laser beam through an acoustooptic cell driven at said predetermined frequency.

4. A method as claimed in claim 1, wherein said scattered second beam portion is passed through said optical lens and then reflected to a beam mixer where it is combined with said first beam portion.

5. A method as claimed in claim 4, wherein said beam mixer is highly transparent to the reflected scattered second beam portion.

6. A method as claimed in claim 5, wherein said first and second beam portions are caused to travel along respective optical paths having substantially the same length.

7. A method as claimed in claim 6, wherein the optical path of said first beam portion has a folded configuration.

8. A method as claimed in claim 7, wherein said first beam portion is reflected by a first mirror onto a second mirror and is then directed to said beam mixer.

9. A method as claimed in claim 8, wherein said first and second mirrors are movable relative to one another to vary the optical path length of said first beam portion in accordance with the optical path length of said second beam portion.

10. A method as claimed in claim 1, wherein step (f) is carried out by passing said electrical fringe signal through an in-phase power divider to divide said signal into first and second signal components, passing said first signal component through a narrow band filter to reject said sidebands without demodulating said phase modulation produced by ambient vibrations and then through a phase shifter to produce a total phase shift of ±90°, mixing said filtered and phase shifted first signal component with said second signal component and passing the resulting signal through a band-pass filter to remove DC and high frequency components and thereby obtain a signal proportional to the surface displacement.

11. A method as claimed in claim 10, wherein use is made of a narrow band filter having a bandwidth of 0.5 to 1 MHz.

12. A method as claimed in claim 10, wherein said electrical fringe signal prior to being passed through said in-phase power divider has an amplitude which is maintained substantially constant.

13. A method as claimed in claim 12, wherein said electrical fringe signal is first passed through a voltage controlled amplifier consisting of a fixed gain amplifier coupled to a voltage controlled attenuator, prior to being passed through said in-phase power divider.

14. A method as claimed in claim 12, wherein said electrical fringe signal is first amplified to a high level and then limited in amplitude by a clipping circuit, prior to being passed through said in-phase power divider.

15. A laser heterodyne interferometric system for measuring the displacement of a free surface of a material subjected to ultrasound, which comprises:
   laser source means for generating a laser beam having a predetermined intensity;
   beam dividing means for dividing said laser beam into first and second beam portions having respective intensities representing minor and major fractions of said predetermined intensity, said first beam portion being angularly displaced relative to said second beam portion and being frequency shifted by a predetermined frequency;
   an optical lens disposed to receive offcenter thereof said second beam portion for focalizing said second beam portion onto the free surface of said material subjected to ultrasound, thereby scattering same;
   beam mixing means for combining the scattered second beam portion with said first beam portion to obtain an optical fringe signal;
   detector means for converting said optical fringe signal into an electrical fringe signal comprising a central peak at said predetermined frequency and a sideband on either side of said central peak; and
   circuitry means for processing said electrical fringe signal without demodulating a phase modulation produced by ambient vibrations, to extract a signal proportional to the displacement of said free surface.

16. A system as claimed in claim 15, wherein said beam dividing means comprises an acoustooptic cell driven at said predetermined frequency.

17. A system as claimed in claim 15, further including reflection means for reflecting said scattered second beam portion past said optical lens to said beam mixing means.

18. A system as claimed in claim 17, wherein said beam mixing means comprises a beam mixer which is highly transparent to the reflected scattered second beam portion.

19. A system as claimed in claim 15, further including reflection means for causing said first and second beam portions to travel along respective optical paths having substantially the same length.

20. A system as claimed in claim 19, wherein said reflection means include a first mirror for reflecting said first beam portion and a second mirror for directing the reflected first beam portion to said beam mixing means.

21. A system as claimed in claim 20, wherein said first and second mirrors are movable relative to one another to vary the optical path length of said first beam portion in accordance with the optical path length of said second beam portion.

22. A system as claimed in claim 15, wherein said circuitry means comprise an in-phase power divider having an input and first and second outputs, the input of said divider being connected to said detector means for dividing said electrical fringe signal into first and second signal components; a narrow band filter having an input and an output, the input of said filter being connected to the first output of said divider for filtering said first signal component to reject said sidebands without demodulating said phase modulation produced by ambient vibrations; a phase shifter having an input and an output, the input of said phase shifter being connected to the output of said narrow band filter for producing a total phase shift of ±90°; a mixer having first and second inputs and an output, the first and second inputs of said mixer being connected respectively to the output of said phase shifter and to the second output of said divider for mixing said filtered and phase shifted first signal component with said second signal component; and a band-pass filter having an input and an output, the input of said band-pass filter being connected to the output of said mixer for filtering the resulting signal to remove DC and high frequency components and thereby obtain a signal proportional to the surface displacement.

23. A system as claimed in claim 22, wherein said narrow band filter has a bandwidth of 0.5 to 1 MHz.

24. A system as claimed in claim 22, further including input circuit means connected intermediate said detector means and said in-phase power divider for maintaining a substantially constant amplitude of said electrical fringe signal.

25. A system as claimed in claim 24, wherein said input circuit means includes a voltage controlled amplifier consisting of a fixed gain amplifier having its output coupled to a voltage controlled attenuator.

26. A system as claimed in claim 24, wherein said input circuit means includes a fixed gain amplifier having its output coupled to a clipping circuit.

* * * * *